US00PP12096P2

(12) United States Plant Patent
Danziger

(10) Patent No.: US PP12,096 P2
(45) Date of Patent: Sep. 18, 2001

(54) NEW GUINEA IMPATIENS PLANT NAMED 'DANHARROYRD'

(75) Inventor: Gabriel Danziger, Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 09/323,148

(22) Filed: Jun. 1, 1999

(51) Int. Cl.[7] ..... A01H 5/00
(52) U.S. Cl. ..... Plt./318
(58) Field of Search ..... Plt./318

(56) References Cited

U.S. PATENT DOCUMENTS

P.P. 7,840 * 3/1992 Kientzler ..... Plt./318

* cited by examiner

*Primary Examiner*—Bruce R. Campell
*Assistant Examiner*—Wendy Anne Baker
(74) *Attorney, Agent, or Firm*—Foley & Lardner

(57) ABSTRACT

A new and distinct cultivar of Impatiens plant named 'Danharroyrd' characterized by having round, red flowers borne above the foliage, vigorous branching, green foliage, and numerous flowers.

1 Drawing Sheet

BACKGROUND OF THE INVENTION

The present invention comprises a new and distinct cultivar of New Guinea Impatiens plant, botanically known as Impatiens, and hereinafter referred to by the cultivar name 'Danharroyrd'.

'Danharroyrd' is a product of a planned breeding program and was originated from a hybridization made by the inventor, Gabriel Danziger, in a controlled breeding program in Mishmar Hashiva, Israel, in 1997. The female parent was an Impatiens cultivar designated A-181. The male parent was an Impatiens cultivar designated B-167. Both parents are proprietary cultivars used in the breeding program.

'Danharroyrd' was discovered and selected as a flowering plant within the progeny of the stated cross by the inventor, Gabriel Danziger, in 1998 in a controlled environment in Mishmar Hashiva, Israel.

The first act of asexual reproduction of 'Danharroyrd' was accomplished when vegetative cuttings were taken from the initial selection in 1998 in a controlled environment in Mishmar Hashiva, Israel, by Gabriel Danziger. The cuttings are apical cuttings. No more than two expanded leaves and 3–4 immature leaves are evident. Horticultural examination of plants grown from these cuttings in Mishmar Hashiva, Israel, has demonstrated that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be basic characteristics of 'Danharroyrd' which in combination distinguish this Impatiens as a new and distinct cultivar:

1. Round, red flowers borne above the foliage;
2. Vigorous branching;
3. Green foliage; and
4. Numerous flowers.

'Danharroyrd' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Mishmar Hashiva, Israel under greenhouse conditions which closely approximate those generally used in commercial practice.

BRIEF DESCRIPTION OF THE DRAWING

The accompanying color photographic drawing shows typical flower and foliage characteristcs of 'Danharroyrd', with colors being as true as possible with illustrations of this type.

DETAILED BOTANICAL DESCRIPTION

The measurements were taken in Mishmar Hashiva, Israel, and are based on plants grown from rooted cuttings in a net-covered greenhouse during the spring at temperatures of 30° C. maximum and 18° C. minimum. In the following description, color references are made to The Royal Horticultural Society Colour Chart (R.H.S.), except where general colors of ordinary significance are used.

Species: *Impatiens hawkeri.*

Classification:

*Botanical.*—A hybrid of the genus Impatiens.

*Commercial.*—New Guinea Impatiens, cv. 'Danharroyrd'.

Plant:

*General appearance and form.*—Height: 15–20 cm. Width: 25–30 cm. Habit: Plant shape is round and compact. Branching: Vigorous in character. Flowering response: 8–9 weeks after planting of rooted cuttings. Flowering season: Throughout the entire year. The plant is an annual plant. It grows in partially shaded areas in temperatures of 10C.–25C. degrees. Lasting quality of bloom: Open during the lifetime of the plant; lastingness of individual flower blooms ranges between 5–10 days after anthesis. Propagation: Leaf-cutting. Rooting: Vigorous, roots initiate in 6–7 days at 25° C. and 8–9 days at 20° C. Stem: Color 46 A; length 20–25 cm; diameter 0.5–1 cm, internode length 3.5–4 cm. Spur color: 53 A. Fragrance: Flowers have no fragrance.

*Foliage.*—Shape of leaf: Lanceolate. Leaf base: Acuminate. Leaf tip: Attenuate. Margin: Shallowly serrated ciliated. Texture: Smooth without pubescence. Length of leaf: 10.5–11 cm. Width of leaf: 3.5–4 cm. Main color on upper surface: Mature leaf: RHS 139 A. Immature leaf: RHS 137 B. Main color on lower surface: Mature leaf: RHS 138 B. Immature leaf: RHS 143 C. Veination: Upper surface: One main, light-red vein RHS 51 A. Lower surface: One main, red vein and small, red veinations (RHS 60B) going from, and parallel to, the main vein.

Inflorescence:

*Corolla.*—Form: 5 petals per flower. Shape: Round. Average number: 20–25 flowers at once per mature plant (four months old). Size: 5–5.5 cm. Petal number: 5. Petal shape: 4 are heart-shaped; the dorsal petals are free, the lateral petals are fused in pairs, the dorsal petal is wider than the lateral petals and is also heart-shaped. Petal color: Upper surface: In spring when opening, petals are red, RHS 45 B, without fading. Lower surface: RHS 52 A.

*Bud.*—Color: 53A. Response: 6–7 weeks after planting of rooted cuttings, developing into open flowers approximately two weeks later. Size before opening: 2–2.5 cm. Aspect: Stands above pedicel and has a curved spur 4 cm long. Pedicel length: 4–4.5 cm. Pedicel color: 53B.

*Reproductive organs.*—Stamens: 1. Anthers: Round, light-red in color. Pollen: White. Stigma: Round, white in color. Ovary: Four-celled, 1 mm in length, green in color.

Disease resistance: This variety is not distinctively resistant or susceptible to plant disease.

Fruit/seeds: The plant produces fruit and seeds. Its fruit is an explosive capsule. Its seeds are smooth, 1 mm width, 2–3 mm length, elliptic shape.

I claim:

1. A new and distinct cultivar of Impatiens plant named 'Danharroyrd', as illustrated and described herein.

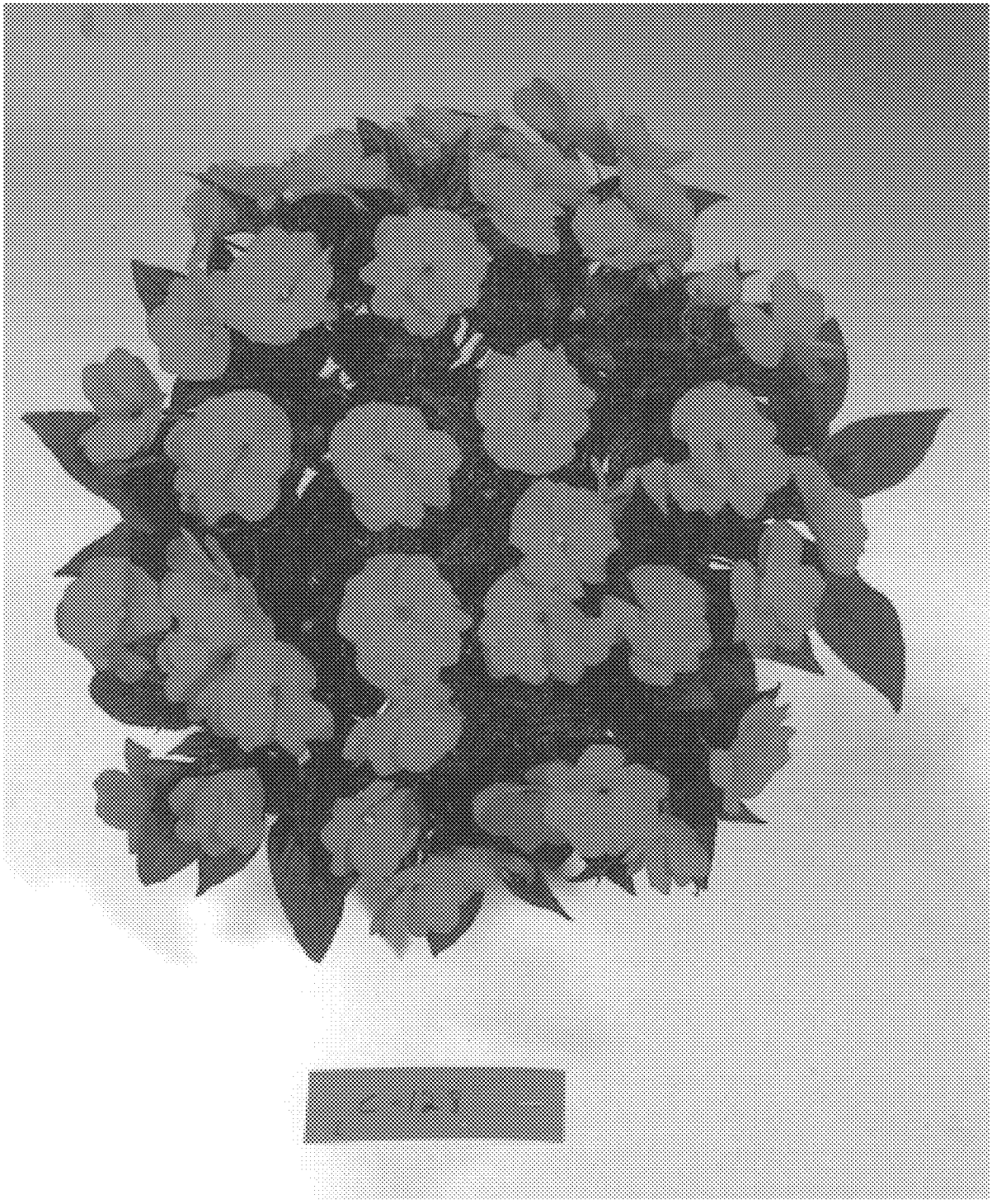

* * * * *